United States Patent [19]

Lin et al.

[11] Patent Number: 5,869,349
[45] Date of Patent: Feb. 9, 1999

[54] IMMOBILIZATION OF ACID-TREATED ANTIBODIES ON SILICEOUS SUPPORT

[75] Inventors: Jinn-Nan Lin, Indianapolis, Ind.; Joseph D. Andrade; I-Nan Chang, both of Salt Lake City, Utah

[73] Assignee: University of Utah Reseach Foundation, Salt Lake City, Utah

[21] Appl. No.: 626,367

[22] Filed: Dec. 12, 1990

[51] Int. Cl.$^6$ .............................. G01N 33/53; C07K 16/00
[52] U.S. Cl. ........................ 436/547; 435/7.94; 435/7.92; 435/7.1; 530/387.1; 530/389.1
[58] Field of Search .................................. 530/387, 388.1, 530/389.1, 391.1; 435/7.2, 7.1, 7.92, 7.94; 436/547

[56] References Cited

U.S. PATENT DOCUMENTS

| | | | |
|---|---|---|---|
| 3,652,761 | 3/1972 | Weetall | 424/12 |
| 4,071,409 | 1/1978 | Messing et al. | 195/63 |
| 5,073,485 | 12/1991 | Amano et al. | 435/7.94 |

OTHER PUBLICATIONS

Ishikawa, et al., J. Immunoassay, 1(3):385–398, 1980.
Conrdie, et al., JIM, 59:289–299, 1983.
Lin et al., JIM, 125:67–77, 1989.

*Primary Examiner*—Susan A. Loring
*Attorney, Agent, or Firm*—Richard P. Fennelly

[57] ABSTRACT

The antigen-binding activity of an antibody immobilized on a siliceous support can be increased by pretreatment of the antibody with acid prior to its immobilization.

10 Claims, No Drawings

IMMOBILIZATION OF ACID-TREATED ANTIBODIES ON SILICEOUS SUPPORT

This invention was made with government support in part under Army Research Office Contract ARO 25539-LS and by the NIH invention.

BACKGROUND OF THE INVENTION

Recently, considerable research efforts have been devoted to the development of fiber-optic immunosensors. An electromagnetic field generated at a silica-liquid interface by total internal reflection, for example, can be used to excite fluorescence of molecules present at the interface (See U.S. Pat. No. 4,447,546). An antibody immobilized at the surface of a silica optical element can bind its complementary antigen from solution, permitting a fast analysis of antigen concentration in the bulk solution. Silica, which is a promising matrix for high pressure affinity chromatography due to its good mechanical stability, which allows for a rapid purification of proteins, has not been used as a common material in conventional immunodiagnostics and immunopurification. Therefore, less work has been done to better understand antibody immobilization on such a surface than on other surfaces.

Although it is known to immobilize antibodies on a siliceous support or carrier, various disclosures exist in regard to maintaining the antibody in an environment which does not irreversibly denature the antibody, namely, a generally alkaline or neutral pH range (See U.S. Pat. Nos. 3,652,761 and 4,071,409 and Anal. Chem. 1980, 52, 2013–2018). U.S. Pat. No. 3,652,761 for example at Col. 6, lines 57–62 indicates that it is "important" that the pH of the solution be held within a range such that the antibody does not become irreversibly denatured.

Ishikawa et al., in J. of Immunoassay, 1(3), 1980, 385–398 reported that an improved preparation of antibody-coated polystyrene beads for a sandwich enzyme immunoassay could be achieved by exposing the antibody to a low pH environment prior to immobilization. Similarly, Conradie et al., in J. of Immunological Methods, 59, (1983) 289–299 reported a similar effect for the antibody coating of polystyrene plates. The Conradie et al. paper indicates that antibodies or antigens bind tightly to plastic surfaces by simple adsorption as contrasted to the use of "other methods" to covalently bind antigens or antibodies to other solid matrices such as "agarose beads, cellulose, nylon, glass, etc."

SUMMARY OF THE INVENTION

The present invention relates to the acid pretreatment of an antibody prior to its immobilization on a siliceous support to increase the antibody binding capacity of the immobilized antibody.

DETAILED DESCRIPTION OF THE INVENTION

The present invention utilizes certain elements which are individually well known to persons of ordinary skill in the art: a siliceous support; an immobilized antibody thereon; and an antigen in solution intended for binding to the immobilized antibody. It is well within the skill of the person in the art to select appropriate components for use herein using the literature available and their level of ordinary skill. It is deemed that the present invention is of general applicability in regard to immobilization of antibodies on siliceous supports.

Representative siliceous supports, for example, include porous silica, wollastonite, silica gel, bentonite, and the like.

Representative antibodies to both large and small (hapten) antigens including proteins, drugs, cells, and toxins include both polyclonal and monoclonal antibodies within the following being mere examples thereof: anti-(human serum albumin) antibody, anti-(red blood cell) antibody, anti-(digoxin) antibody, and anti-(human chorionic gonadotropin) antibody.

The instant invention relates to the treatment of the selected antibody to a buffered acid pH (e.g., a pH of from about 2 to about 4) for a sufficient length of time (e.g., from about one to about sixty minutes) to denature the antibody to a sufficient degree to result in the desired degree of increase in the antigen-binding activity of the antibody. The treated antibody is then immobilized to the siliceous support by either adsorption or covalent coupling. If covalent coupling is chosen, a wide variety of known methods can be employed including the derivatization of the silica support with the following functionalities: benzoyl azide; bromoacetamide; azidoaryl; aldehyde; isothiocyanate; diazonium salt; acid chloride; active ester; iminocarbonate; hydrazide; epoxy; and amine.

The present invention is illustrated by the Examples which follow.

EXPERIMENTAL PROCEDURE FOR EXAMPLES

1. Cleaning of silica samples

All silica samples were cut from 2.5 cm×2.5 cm×0.1 cm fused silica slides (CO grade, ESCO), and the edges were finely polished. The size of each sample was 2.4 cm×0.955 cm×0.1 cm and fitted into a 13×75 mm culture tube (Fisher) in which all surface reactions took place at room temperature. A beaker containing test tubes with silica samples inside was first immersed in hot chromic acid at 80° C. for thirty minutes and was then thoroughly rinsed in purified deionized water filtered through a Milli-Q ultrafiltration system (Millipore). Care was taken to avoid touching anything inside the container. The glassware and samples were dried in a desiccator at 120° C. for more than two hours. After drying, one of the newly cleaned samples was checked by the Wilhelmy plate water contact angle technique (Andrade et al., Surface and Interfacial Aspects of Biomedical Polymers, Vol. 1, Surface Chemistry and Physics, Plenum Press, New York, p. 262) to ensure the cleanliness of the surfaces.

2. Silanization of cleaned silica samples

Two silane reagents were used in this study: 3-aminopropyltriethoxy silane (APS, Aldrich) and dimethyldichloro silane (DDS, Petrarch). The silica samples or chips were reacted with an aqueous solution of APS (5% APS and 95% deionized water v/v) or with a dry toluene solution of DDS (10% v/v DDS and 90% v/v toluene) for fifteen and thirty minutes at room temperature, respectively. The APS samples were rinsed thoroughly with deionized water and absolute ethanol, and the DDS samples were rinsed with absolute ethanol. The chips were then cured in a vacuum oven (which has been flushed with nitrogen three times) at 120° to 130° C. for one hour.

3. Antibody and antigen system

Polyclonal goat anti-human serum albumin (anti-HSA) IgG fraction was purchased from Cappel Laboratories. Crystallized human serum albumin (HSA) was purchased from Miles Diagnostics.

Murine monoclonal antifluorescyl (9-40) IgG1 and (4-4-20) IgG2 were also utilized. The antigen used in this case was FITC-BSA-I-125 (degree of labelling of FITC was 10 from Sigma).

4. Radiolabelling of Proteins

The anti-HSA, HSA, or the FITC-BSA was labelled with carrier-free I-125 (100 mCi/ml, Amersham) by a modification of the chloramine-T method as described by Chuang et al. (J. Lab. Clin. Med. (1978) 92, 483). Centrifugation of 4 cm high Sephadex G-25 coarse grade resin (Pharmacia) minicolumns having 0.3 ml of iodinated protein solution has provided a rapid and simple means to separate the unbound iodide Tuszynski et al., 1980, Anal. Biochem. 106, 118). The final concentration of $^{125}$I-protein was measured in a UV-visible spectrophotometer (Beckman, Model 35) at 280 nm. Values of 0.54 and 66,000 were used for the absorption extinction coefficient ($E^{0.1\%}$) and the molecular weight (MW) of HSA, respectively; while for IgG the values used for $E^{0.1\%}$ and MW were 1.35 and 150,000, respectively. The values of 0.66 and 66,000 were used as the $E^{0.1\%}$ and MW values for BSA. Labelling efficiency was determined by precipitating proteins with 20% trichloroacetic acid (TCA from Sigma) in the presence of BSA as the carrier protein. The amount of iodide bound to protein was determined by subtracting the counts in the supernatant from the total counts in solution collected from the Sephadex column.

5. Preparation of the Partially Denatured Antibody

Ab was partially denatured by dissolving approximately 10 mg of anti-HSA or antifluorescyl 4-4-20 or 9-40 antibodies in 1 ml of 0.1M citric acid/phosphate (CP) buffer (pH 2.8) for various lengths of time. The pH of the Ab solution was then increased by using a prepacked Sephadex G-25M column (Pharmacia) which has been equilibrated with the buffer used for Ab immobilization. A Millipore filter (0.22 $\mu$m) was used to remove the Ab aggregates in the solution.

6. Immobilization of Antibody 6.1. Silica

Two types of Ab immobilization were performed on silica surfaces: (1) physical adsorption of Ab in 0.15M phosphate buffered saline (PBS) pH 7.4 onto DDS treated silica surfaces for various lengths of time followed by thorough rinsing with PBS, (2) covalent immobilization; the APS samples were reacted with 2.5% glutaraldehyde (Glu, E. M. grade, Polysciences) in 0.1M carbonate-bicarbonate (CB) buffer pH 9.2 for two hours followed by rinsing with CB buffer. The Glu surfaces were then reacted with the Ab solution in CB buffer, for various lengths of time. The Ab-coupled samples were washed with CB buffer and the remaining aldehyde groups on the surfaces were deactivated with 0.2M ethanolamine (Aldrich) for one hour. For both surfaces, the Ab solution concentration used was 0.7 to 0.9 mg/ml. Surface concentrations of the immobilized Abs (native or denatured) were determined by a radiolabelling technique.

6.2. Hydrogel

An Affi-Gel Hz agarose gel, purchased from Bio-Rad, was used to immobilize anti-HSA. The gel contained hydrazide groups which reacted with aldehydes of oxidized carbohydrates on the Ab to form covalent hydrazone bonds. The coupling procedures used involved the initial washing of an aliquot of the gel slurry with diluted coupling buffer, pH 5.5, to remove isopropanol. Sodium periodate stock solution (20 mg/ml) was added to Ab solution (1.5 mg/ml) at one-tenth the final volume. The mixture was gently mixed for one hour at room temperature, and the sodium periodate was then removed using a desalting column which has been washed and equilibrated with diluted coupling buffer, pH 5.5. The oxidized Ab was transferred to the gel in the reaction tube and gently shaken for twenty hours at room temperature. The amount of Ab immobilized on the gel beads was determined by measuring the depletion of Ab in bulk solution.

7. Competitive immobilization

In this study equal amounts of native and denatured (one hour) Abs (0.8 mg/ml) were mixed prior to the immobilization onto DDS and Glu surfaces. The Ab immobilization time was three hours for both DDS and Glu surfaces. Surface concentration of each of the Abs was determined separately by radiolabelling one of the Abs at a time.

8. Antibody-Antigen Binding Experiments

Ag binding capacities (Ag BC) of the native and denatured Abs in solution and on the surfaces were also determined. For the solution case, a method described by Minden et al. in Immunochemistry 12, 477(1975) was used. All 0.5 ml microfuge vials were precoated with bovine serum albumin (BSA, Miles Diagnostics) to minimize nonspecific adsorption followed by rinsing with PBS. Radiolabelled HSA was incubated with unlabelled native or denatured Ab in the vial for one hour at room temperature. Then a minimum amount of secondary Ab, rabbit anti-goat IgG (anti-G IgG, Cappel Laboratories), required for precipitation of the anti-HSA was added to all vials. The precipitate was allowed to form by incubating the solution at 4° C. overnight. All samples were then centrifuged at 18,000 rpm (Fisher, Model 235A) for fifteen minutes, and an aliquot of supernatant was counted. The amount of bound Ag was obtained by calculating the difference between the total counts added initially and the supernatant after centrifugation.

In the case of solid phase immunoassay, the anti-HSA- or antifluorescyl coated surfaces were incubated with an excess of iodinated HSA for one hour at room temperature. The silica samples were held by forceps and were rinsed with PBS buffer gently to remove the weakly adsorbed Ag solution layer. The hydrogel samples were rinsed more than five times until no iodinated HSA was detected in the rinsing solution. The specificity of the immobilized Ab on different surfaces was determined by adding an excess amount of BSA to the Ag solution. The amount of BSA added was seventy times higher than that of HSA or FITC-BSA-I-125. All experiments performed in this study were at least duplicated.

9. Fluorescence Measurement

The kinetics of fluorescence intensity of the anti-HSA in PBS (pH 7.4) and CP buffer (pH 2.8) was also measured. To ensure rapid mixing of the Ab and buffer, 0.1 ml of Ab dissolved in PBS buffer was first added to the bottom of an 1.5 ml cuvette. The solution was then diluted ten times by adding either PBS or CP buffer rapidly to the cuvette to give a final Ab concentration around $1.5 \times 10^{-6}$M. The Ab was excited with a polarized 280 nm light from a broadband 150 W Xe high pressure lamp (ILC Technology). The fluorescence at 340 nm was collected at 90° C. with respect to the incident light by an emission monochromator (HR 640, Instruments SA).

EXAMPLE 1

The Table set forth below shows the antigen (Ag) binding of immobilized polyclonal antibody (Ab) on dimethyldichloro-silane (DDS) and glutaraldehyde (Glu) surfaces as a function of Ab denaturation time in pH 2.8 buffer. The pH of the Ab solution was increased to pH 7.4 for the DDS surface and pH 9.2 for the Glu surface just prior to immobilization. Bovine serum albumen (BSA) was used in excess to minimize nonspecific binding of human serum albumen (HSA) in this and all Examples which follow.

| Anti-HSA Denatur. Time (min) | Bound $^{125}$I-HSA ($10^{-13}$ mole/cm$^2$) | |
|---|---|---|
| | on DDS | on Glu |
| 0* | 6.0 ± 0.07 | 2.8 ± 0.16 |
| 1 | 10.1 ± 0.02 | 4.0 ± 0.09 |
| 20 | 11.0 ± 0.28 | 4.2 ± 0.14 |
| 60 | 9.0 ± 0.22 | 6.2 ± 0.28 |
| 300 | 5.2 ± 0.25 | 5.2 ± 0.26 |

*Control (native, undenatured, non-acid treated Ab).

On the DDS surface, the Ag BC for the twenty minute case was approximately two times higher than that for the control (native Ab) case. The increase in Ag binding was deemed to be due to specific interactions because the non-specific binding area was deemed to be blocked by BSA. Furthermore, the Ag BC decreased dramatically with increasing denaturation time. The five hour denaturation period showed a slightly lower Ag BC than the native case. A similar trend is also observed on Glu surfaces. The Ag BC increased with increasing Ab denaturation time and reached a maximum at one hour which showed approximately two times higher in Ag BC than the native Ab.

EXAMPLE 2

The solution activities of native Ab and Ab denatured for one hour were also determined. The purpose of this experiment was to demonstrate the effect of acid treatment on Ab activity in solution. The results indicate that the denatured Ab retains 75% activity in comparison with the native Ab:

| Antibodies$^a$ | Bound HSA × $10^{-7}$M |
|---|---|
| Native | 1.4 ± 0.0 |
| Denatured (one hour) | 1.0 ± 0.0 |

$^a$Ab concentration: 1.1 × $10^{-7}$M for both Abs.

EXAMPLE 3

The Ag BC of denatured Ab (twenty minutes) on DDS surfaces as a function of the Ab solution storage time is given in the Table (from FIG. 5) which follows:

| Anti-HSA Solution Storage Time (hrs) | Bound $^{125}$I-HSA ($10^{-13}$ mole/cm$^2$) |
|---|---|
| 0 | 11.0 |
| 50 | 10.5 |
| 100 | 10.25 |
| 150 | 10.0 |

For the zero time data, the denatured Ab was immobilized immediately after PBS exchange in the denaturation process. The same solution was then stored at 4° C. and its Ag BC on the surfaces was measured for various lengths of storage time. It is well known that denatured protein sometimes can renature back to its original conformation under suitable conditions (Ghelis et al., Simulation of Protein Folding: Studies of In Vitro Denaturation—Renaturation. In: Protein Folding. Academic Press, New York, Ch. 5). Since the Ab adsorption took place at pH 7.4, it is important to know the change of the denatured Ab during the three hour adsorption period. The results shown in the Table indicate that the Ag BC of the Ab on DDS surfaces decreased linearly from 11 to 10×$10^{-13}$ mole/cm$^2$ over a six day period. The decrease accounts for about 10% of the total Ag BC. This suggests that as far as the Ag BC is concerned, the properties of the denatured Ab were relatively constant during the adsorption process.

EXAMPLE 4

The surface concentration of Ab immobilized on DDS and Glu surfaces was also determined as a function of Ab denaturation time in low pH buffer. The results show that the amount of adsorbed Ab increased rapidly with increasing denaturation time and reached a maximum at twenty minutes on the DDS surfaces and one hour on the Glu surfaces. The Ab surface concentrations then decreased gradually with further increases in denaturation time:

| Anti-HSA Denatur. Time (min) | Adsorbed anti-HSA ($10^{-12}$ mole/cm$^2$) | |
|---|---|---|
| | on DDS | on Glu |
| 0 | 2.5 ± 0.13 | 2.1 ± 0.36 |
| 1 | 5.5 ± 0.02 | 3.1 ± 0.45 |
| 20 | 7.8 ± 0.18 | 3.1 ± 0.42 |
| 60 | 6.6 ± 0.31 | 3.8 ± 0.57 |
| 300 | 5.3 ± 0.10 | 3.0 ± 0.04 |

EXAMPLE 5

The Ab surface concentration and its Ag BC on the Affi-Gel beads were determined using the oxidized Abs. The Ab denatured for one hour was used:

| | Ab. Surf. Conc. | | Ag Bind. Capac. | |
|---|---|---|---|---|
| Surfaces | Denat. Ab | Native Ab | Denat. Ab | Native Ab |
| DDS ($10^{12}$/cm$^2$) | 6.6 | 2.5 | 0.90 | 0.60 |
| Glu ($10^{12}$/cm$^2$) | 3.8 | 2.1 | 0.62 | 0.28 |
| Hydrogel ($10^{-5}$/0.2 ml gel) | 1.1 | 1.0 | 1.3 | 1.6 |

The surface concentration of denatured Ab were slightly higher than that for the native Ab, whereas the opposite situation was observed for the Ag BC. The Table also lists one hour data (taken from the data in Examples 1 and 4) for DDS and Glu surfaces for comparison. It is apparent that Abs on silica and hydrogel surfaces behave differently. The properties of the Abs on hydrogel surfaces are similar to that in solution. The low Ag BC of denatured Ab compared to the native Ab results from acid treatment.

EXAMPLE 6

It is well known that proteins in low pH solution will undergo conformational changes, which in turn affect their adsorption properties. This phenomenon is clearly demonstrated by the results shown in the following two Tables. First, the kinetics of Ab denaturation in low pH solution was monitored by measuring the intrinsic fluorescence at 340 nm (Ghelis et al., supra).

This illustrates the kinetics of relative fluorescence intensity of anti-HSA in pH 7.4 PBS buffer and pH 2.8 CP buffer at 340 nm. The data for pH 2.8 shows a trend of increasing normalized fluorescence demonstrating the denaturation phenomenon of the Ab in low pH solution. The data for pH 7.4 PBS buffer indicates that complete mixing was achieved. The normalized fluorescence was fluorescence intensity at any time (F.I.(t)) divided by the initial fluorescence (F.I.(t)):

|  | Normalized Fluorescence | |
| --- | --- | --- |
| Time (sec) | pH 2.8 | pH 7.4 |
| 0 | 1.00 | 1.00 |
| 5 | 1.09 | 0.99 |
| 10 | 1.12 | 0.99 |
| 15 | 1.13 | 0.99 |
| 20 | 1.13 | 1.00 |
| 25 | 1.14 | 1.01 |
| 30 | 1.15 | 0.98 |
| 35 | 1.16 | 0.97 |
| 40 | 1.16 | 0.97 |
| 45 | 1.19 | 0.97 |
| 50 | 1.20 | 0.97 |
| 60 | 1.23 | 0.97 |
| 70 | 1.23 | 0.98 |
| 80 | 1.24 | 0.97 |
| 90 | 1.26 | 0.97 |
| 100 | 1.26 | 0.97 |
| 110 | 1.27 | 0.97 |
| 120 | 1.28 | 0.97 |
| 130 | 1.29 | — |
| 140 | 1.30 | — |
| 150 | 1.30 | — |
| 160 | 1.32 | — |
| 170 | 1.32 | — |
| 180 | 1.33 | — |
| 190 | 1.33 | — |
| 200 | 1.33 | — |

It was observed that the fluorescence intensity increased nearly 1.4 times over the period of four minutes. Furthermore, there was approximately another 25% increase at the end of three hours, which is not shown in the data presented above in the Table. Since proper mixing is important in this study, a control experiment was done by diluting the small aliquot of Ab with PBS buffer. A constant fluorescence indicated that complete mixing was achieved. Therefore, the increase in fluorescence intensity in the case of low pH is an indication of conformational change of the Ab.

EXAMPLE 7

The results of competitive adsorption of native and denatured (one hour) on DDS and Glu surfaces are listed in the following Table:

|  | Ab Surface Conc. ($\times 10^{-12}$ mole/cm$^2$) | |
| --- | --- | --- |
| Type of Ab | on DDS | on Glu |
| Native Ab | 0.7 ± 0.0 | 0.5 ± 0.07 |
| Denatured Ab (1 hr) | 5.4 ± 0.1 | 2.2 ± 0.15 |

It was apparent that the denatured Ab had a much higher affinity to both surfaces than the native Ab.

EXAMPLE 8

The following Table illustrates the results obtained using murine monoclonal anti-fluorescyl (4-4-20) IgG2 as the antibody on a DDS-treated silica surface for various storage times for native (N), denatured for five minutes (D5), and denatured for one hour (D60):

| Storage Time | FI-BSA-$^{125}$I-bound ($\times 10^{-13}$ mole/cm$^2$) | | |
| --- | --- | --- | --- |
| (hrs) | N | D5 | D60 |
| 0 | 2.7 ± 0.58 | 4.3 ± 0.40 | 11.2 ± 0.84 |
| 4 | 2.4 ± 0.05 | 3.0 ± 0.05 | 7.0 ± 0.35 |
| 21 | 2.2 ± 0.01 | 2.1 ± 0.01 | 4.3 ± 0.01 |

EXAMPLE 9

This data is analogous to that in Example 8 for murine monoclonal anti-fluorescyl (9-40) IgG1 which was denatured for sixty minutes:

| Storage Time | FI-BSA-$^{125}$I-bound ($\times 10^{-3}$ mole/cm$^2$) | |
| --- | --- | --- |
| (hrs) | N | D60 |
| 0 | 5.3 ± 0.71 | 22.2 ± 1.10 |
| 3 | 4.6 ± 0.28 | 17.3 ± 0.64 |
| 6 | — | 16.5 ± 0.42 |
| 20 | 4.8 ± 0.55 | 14.7 ± 0.57 |

The foregoing Examples are presented to illustrate only certain embodiments of the invention and should not be construed in a limiting sense for that reason. The scope of protection sought is set forth in the claims which follow.

We claim:

1. A method for increasing the antigen-binding activity of an antibody that is immobilized on a siliceous support which comprises pretreating the antibody with acid prior to its immobilization to increase the antigen-binding capacity.

2. The method of claim 1 wherein the antibody is polyclonal.

3. The method of claim 1 wherein the antibody is monoclonal.

4. The method as claimed in claim 1 wherein the acid pretreatment is performed at a pH of from about 2 to about 4.

5. The method as claimed in claim 1 wherein the acid pretreatment is performed at a pH of from about 2 to about 4 for a time ranging from about one minute to sixty minutes.

6. The method as claimed in claim 5 wherein the antibody is polyclonal.

7. The method as claimed in claim 5 wherein the antibody is monoclonal.

8. In combination, a siliceous support having immobilized thereon a partially denatured, acid-treated antibody.

9. The combination of claim 8 wherein the antibody is polyclonal.

10. The combination of claim 8 wherein the antibody is monoclonal.

* * * * *